(12) United States Patent
Fuglsang

(10) Patent No.: US 6,355,228 B1
(45) Date of Patent: Mar. 12, 2002

(54) ORAL CARE PRODUCT COMPRISING A MUTAN BINDING DOMAIN

(75) Inventor: Claus Crone Fuglsang, Niva (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/295,744

(22) Filed: Apr. 20, 1999

Related U.S. Application Data

(63) Continuation of application No. PCT/DK97/00470, filed on Oct. 27, 1997.

(30) Foreign Application Priority Data

Oct. 25, 1996 (DK) ............................................. 1186/96

(51) Int. Cl.$^7$ .......................... A61K 7/25; A61K 38/46; C12N 9/24; C12N 1/20; C07H 21/04
(52) U.S. Cl. ................... 424/50; 424/94.6; 424/192.1; 435/200; 435/252.3; 435/320.1; 435/189; 435/192; 435/195; 435/198; 435/201; 435/203; 435/204; 435/205; 435/219; 435/231; 536/23.4
(58) Field of Search ...................... 424/50, 94.6, 192.1, 424/183; 435/200–205, 252.3, 320.1, 189, 192, 195, 198, 219, 231; 536/23.4

(56) References Cited

U.S. PATENT DOCUMENTS 4,353,891 A  10/1982  Guggenheim et al. ........ 424/50

FOREIGN PATENT DOCUMENTS

| WO | WO 93/21331 | 10/1993 |
| WO | WO 95/31556 | 11/1995 |
| WO | WO 97/29197 | 8/1997 |

OTHER PUBLICATIONS

Elsevier Sci. Pub. R.V., pp. 121–126 (1991).
TIBTECH, vol. 7, pp. 239–243 (1989).

Primary Examiner—Ponnathapu Achutamurthy
Assistant Examiner—Tekchand Saidha
(74) Attorney, Agent, or Firm—Elias J. Lambiris

(57) ABSTRACT

Disclosed is a polypeptide hybrid containing an amino acid sequence with binding affinity for mutan, the amino acid sequence being bound to an active component useful for oral care purposes; an oral care composition comprising a mutan binding domain; an oral care product comprising such an oral care composition of the invention; and finally the use of a mutan binding polypeptide hybrid or a single unit MBD for oral care purposes, including preventing dental plaque formation and/or removal of existing dental plaque.

8 Claims, 3 Drawing Sheets

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
       (A) LENGTH: 1905 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (B) STRAIN: Trichoderma harzianum CBS 243.71

(ix) FEATURE:
       (A) NAME/KEY: sig_peptide
       (B) LOCATION:1..120

(xi) SEQUENCE DESCRIPTION: SEQ ID NO: 1:

```
ATG TTG GGC GTT GTC CGC CGT CTA GGC CTA GGC GCC CTT GCT GCC GCA   48
Met Leu Gly Val Val Arg Arg Leu Gly Leu Gly Ala Leu Ala Ala Ala
 1               5                  10                  15

GCT CTG TCT TCT CTC GGC AGT GCC GCT CCC GCC AAT GTT GCT ATT CGG   96
Ala Leu Ser Ser Leu Gly Ser Ala Ala Pro Ala Asn Val Ala Ile Arg
                20                  25                  30

TCT CTC GAG GAA CGT GCT TCT TCT GCT GAC CGT CTC GTA TTC TGT CAC  144
Ser Leu Glu Glu Arg Ala Ser Ser Ala Asp Arg Leu Val Phe Cys His
            35                  40                  45

TTC ATG ATT GGT ATT GTT GGT GAC CGT GGC AGC TCA GCA GAC TAT GAT  192
Phe Met Ile Gly Ile Val Gly Asp Arg Gly Ser Ser Ala Asp Tyr Asp
        50                  55                  60

GAT GAC ATG CAA CGT GCC AAA GCC GCT GGC ATT GAC GCA TTC GCT CTG  240
Asp Asp Met Gln Arg Ala Lys Ala Ala Gly Ile Asp Ala Phe Ala Leu
 65                  70                  75                  80

AAC ATC GGC GTT GAC GGC TAT ACC GAC CAG CAA CTC GGG TAT GCC TAT  288
Asn Ile Gly Val Asp Gly Tyr Thr Asp Gln Gln Leu Gly Tyr Ala Tyr
                85                  90                  95

GAC TCT GCC GAC CGT AAT GGC ATG AAA GTC TTC ATT TCA TTC GAT TTC  336
Asp Ser Ala Asp Arg Asn Gly Met Lys Val Phe Ile Ser Phe Asp Phe
            100                 105                 110

AAC TGG TGG AGC CCC GGT AAT GCA GTT GGT GTT GGC CAG AAG ATT GCG  384
Asn Trp Trp Ser Pro Gly Asn Ala Val Gly Val Gly Gln Lys Ile Ala
        115                 120                 125

CAG TAT GCC AGC CGT CCC GCC CAG CTG TAT GTT GAC AAC CGG CCA TTC  432
Gln Tyr Ala Ser Arg Pro Ala Gln Leu Tyr Val Asp Asn Arg Pro Phe
130                 135                 140

GCC TCT TCC TTC GCT GGT GAC GGT TTG GAT GTA AAT GCG TTG CGC TCT  480
Ala Ser Ser Phe Ala Gly Asp Gly Leu Asp Val Asn Ala Leu Arg Ser
145                 150                 155                 160

GCT GCA GGC TCC AAC GTT TAC TTT GTG CCC AAC TTC CAC CCT GGT CAA  528
Ala Ala Gly Ser Asn Val Tyr Phe Val Pro Asn Phe His Pro Gly Gln
                165                 170                 175

TCT TCC CCC TCC AAC ATT GAT GGC GCC CTC AAC TGG ATG GCC TGG GAT  576
Ser Ser Pro Ser Asn Ile Asp Gly Ala Leu Asn Trp Met Ala Trp Asp
            180                 185                 190

AAT GAT GGA AAC AAC AAG GCA CCC AAG CCG GGC CAG ACT GTC ACG GTG  624
Asn Asp Gly Asn Asn Lys Ala Pro Lys Pro Gly Gln Thr Val Thr Val
        195                 200                 205
```

```
GCA GAC GGT GAC AAC GCT TAC AAG AAT TGG TTG GGT GGC AAG CCT TAC 672
Ala Asp Gly Asp Asn Ala Tyr Lys Asn Trp Leu Gly Gly Lys Pro Tyr
    210                 215                 220

CTA GCG CCT GTC TCC CCT TGG TTT TTC ACC CAT TTT GGC CCT GAA GTT 720
Leu Ala Pro Val Ser Pro Trp Phe Phe Thr His Phe Gly Pro Glu Val
225                 230                 235                 240

TCA TAT TCC AAG AAC TGG GTC TTC CCA GGT GGT CCT CTG ATC TAT AAC 768
Ser Tyr Ser Lys Asn Trp Val Phe Pro Gly Gly Pro Leu Ile Tyr Asn
                245                 250                 255

CGG TGG CAA CAG GTC TTG CAG CAG GGC TTC CCC ATG GTT GAG ATT GTT 816
Arg Trp Gln Gln Val Leu Gln Gln Gly Phe Pro Met Val Glu Ile Val
            260                 265                 270

ACC TGG AAT GAC TAC GGC GAG TCT CAC TAC GTC GGT CCT CTG AAG TCT 864
Thr Trp Asn Asp Tyr Gly Glu Ser His Tyr Val Gly Pro Leu Lys Ser
        275                 280                 285

AAG CAT TTC GAT GAT GGC AAC TCC AAA TGG GTC AAT GAT ATG CCC CAT 912
Lys His Phe Asp Asp Gly Asn Ser Lys Trp Val Asn Asp Met Pro His
    290                 295                 300

GAT GGA TTC TTG GAT CTT TCA AAG CCG TTT ATT GCT GCA TAT AAG AAC 960
Asp Gly Phe Leu Asp Leu Ser Lys Pro Phe Ile Ala Ala Tyr Lys Asn
305                 310                 315                 320

AGG GAT ACT GAT ATA TCT AAG TAT GTT CAA AAT GAG CAG CTT GTT TAC1008
Arg Asp Thr Asp Ile Ser Lys Tyr Val Gln Asn Glu Gln Leu Val Tyr
                325                 330                 335

TGG TAC CGC CGC AAC TTG AAG GCA TTG GAC TGC GAC GCC ACC GAC ACC1056
Trp Tyr Arg Arg Asn Leu Lys Ala Leu Asp Cys Asp Ala Thr Asp Thr
            340                 345                 350

ACC TCT AAC CGC CCG GCT AAT AAC GGA AGT GGC AAT TAC TTT ATG GGA1104
Thr Ser Asn Arg Pro Ala Asn Asn Gly Ser Gly Asn Tyr Phe Met Gly
        355                 360                 365

CGC CCT GAT GGT TGG CAA ACT ATG GAT GAT ACC GTT TAT GTT GCC GCA1152
Arg Pro Asp Gly Trp Gln Thr Met Asp Asp Thr Val Tyr Val Ala Ala
    370                 375                 380

CTT CTC AAG ACC GCC GGT AGC GTC ACG GTC ACG TCT GGC GGC ACC ACT1200
Leu Leu Lys Thr Ala Gly Ser Val Thr Val Thr Ser Gly Gly Thr Thr
385                 390                 395                 400

CAA ACG TTC CAG GCC AAC GCC GGA GCC AAC CTC TTC CAA ATC CCT GCC1248
Gln Thr Phe Gln Ala Asn Ala Gly Ala Asn Leu Phe Gln Ile Pro Ala
                405                 410                 415

AGC ATC GGC CAG CAA AAG TTT GCT CTA ACT CGC AAC GGT CAG ACC GTC1296
Ser Ile Gly Gln Gln Lys Phe Ala Leu Thr Arg Asn Gly Gln Thr Val
            420                 425                 430

TTT AGC GGA ACC TCA TTG ATG GAT ATC ACC AAC GTT TGC TCT TGC GGT1344
Phe Ser Gly Thr Ser Leu Met Asp Ile Thr Asn Val Cys Ser Cys Gly
        435                 440                 445

ATC TAC AAT TTC AAC CCA TAT GTT GGC ACC ATT CCT GCC GGC TTT GAC1392
Ile Tyr Asn Phe Asn Pro Tyr Val Gly Thr Ile Pro Ala Gly Phe Asp
    450                 455                 460

GAC CCT CTT CAG GCT GAC GGT CTT TTC TCT TTG ACC ATC GGA TTG CAT1440
Asp Pro Leu Gln Ala Asp Gly Leu Phe Ser Leu Thr Ile Gly Leu His
465                 470                 475                 480

GTC ACG ACT TGT CAG GCC AAG CCA TCT CTT GGA ACC AAC CCT CCT GTC1488
Val Thr Thr Cys Gln Ala Lys Pro Ser Leu Gly Thr Asn Pro Pro Val
                485                 490                 495

ACT TCT GGC CCT GTG TCC TCG CTG CCA GCT TCC TCC ACC ACC CGC GCA1536
Thr Ser Gly Pro Val Ser Ser Leu Pro Ala Ser Ser Thr Thr Arg Ala
            500                 505                 510

TCC TCG CCT CCT GTT TCT TCA ACT CGT GTC TCT TCT CCC CCT GTC TCT1584
Ser Ser Pro Pro Val Ser Ser Thr Arg Val Ser Ser Pro Pro Val Ser
        515                 520                 525
```

```
          TCC CCT CCA GTT TCT CGC ACC TCT TCT CCC CCT CCC CCT CCG GCC AGC 1632
          Ser Pro Pro Val Ser Arg Thr Ser Ser Pro Pro Pro Pro Pro Ala Ser
                  530                 535                 540

AGC ACG CCG CCA TCG GGT CAG GTT TGC GTT GCC GGC ACC GTT GCT GAC 1680
          Ser Thr Pro Pro Ser Gly Gln Val Cys Val Ala Gly Thr Val Ala Asp
          545                 550                 555                 560

GGC GAG TCC GGC AAC TAC ATC GGC CTG TGC CAA TTC AGC TGC AAC TAC 1728
          Gly Glu Ser Gly Asn Tyr Ile Gly Leu Cys Gln Phe Ser Cys Asn Tyr
                          565                 570                 575

GGT TAC TGT CCA CCG GGA CCG TGT AAG TGC ACC GCC TTT GGT GCT CCC 1776
          Gly Tyr Cys Pro Pro Gly Pro Cys Lys Cys Thr Ala Phe Gly Ala Pro
                      580                 585                 590

ATC TCG CCA CCG GCA AGC AAT GGG CGC AAC GGC TGC CCT CTA CCG GGA 1824
          Ile Ser Pro Pro Ala Ser Asn Gly Arg Asn Gly Cys Pro Leu Pro Gly
                          595                 600                 605

GAA GGC GAT GGT TAT CTG GGC CTG TGC AGT TTC AGT TGT AAC CAT AAT 1872
          Glu Gly Asp Gly Tyr Leu Gly Leu Cys Ser Phe Ser Cys Asn His Asn
                      610                 615                 620

TAC TGC CCG CCA ACG GCA TGC CAA TAC TGT TAG                     1905
          Tyr Cys Pro Pro Thr Ala Cys Gln Tyr Cys *
          625                 630                 635
```

(2) INFORMATION FOR SEQ ID NO: 2:

(i) SEQUENCE CHARACTERISTICS:
        (A) LENGTH: 634 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Gly Val Val Arg Arg Leu Gly Leu Gly Ala Leu Ala Ala Ala
 1               5                  10                  15

Ala Leu Ser Ser Leu Gly Ser Ala Ala Pro Ala Asn Val Ala Ile Arg
                20                  25                  30

Ser Leu Glu Glu Arg Ala Ser Ser Ala Asp Arg Leu Val Phe Cys His
            35                  40                  45

Phe Met Ile Gly Ile Val Gly Asp Arg Gly Ser Ser Ala Asp Tyr Asp
 50                  55                  60

Asp Asp Met Gln Arg Ala Lys Ala Ala Gly Ile Asp Ala Phe Ala Leu
 65                  70                  75                  80

Asn Ile Gly Val Asp Gly Tyr Thr Asp Gln Gln Leu Gly Tyr Ala Tyr
                    85                  90                  95

Asp Ser Ala Asp Arg Asn Gly Met Lys Val Phe Ile Ser Phe Asp Phe
                100                 105                 110

Asn Trp Trp Ser Pro Gly Asn Ala Val Gly Val Gly Gln Lys Ile Ala
            115                 120                 125

Gln Tyr Ala Ser Arg Pro Ala Gln Leu Tyr Val Asp Asn Arg Pro Phe
130                 135                 140

Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
                180                 185                 190

Asn Asp Gly Asn Asn Lys Ala Pro Lys Pro Gly Gln Thr Val Thr Val
            195                 200                 205
```

```
Ala Asp Gly Asp Asn Ala Tyr Lys Asn Trp Leu Gly Gly Lys Pro Tyr
210                     215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Pro Leu Ile Tyr Asn
                245                 250                 255

Arg Trp Gln Gln Val Leu Gln Gln Gly Phe Pro Met Val Glu Ile Val
            260                 265                 270

Thr Trp Asn Asp Tyr Gly Glu Ser His Tyr Val Gly Pro Leu Lys Ser
            275                 280                 285

Lys His Phe Asp Asp Gly Asn Ser Lys Trp Val Asn Asp Met Pro His
        290                 295                 300

Asp Gly Phe Leu Asp Leu Ser Lys Pro Phe Ile Ala Ala Tyr Lys Asn
305                 310                 315                 320

Arg Asp Thr Asp Ile Ser Lys Tyr Val Gln Asn Glu Gln Leu Val Tyr
                325                 330                 335

Trp Tyr Arg Arg Asn Leu Lys Ala Leu Asp Cys Asp Ala Thr Asp Thr
            340                 345                 350

Thr Ser Asn Arg Pro Ala Asn Asn Gly Ser Gly Asn Tyr Phe Met Gly
            355                 360                 365

Arg Pro Asp Gly Trp Gln Thr Met Asp Asp Thr Val Tyr Val Ala Ala
370                 375                 380

Leu Leu Lys Thr Ala Gly Ser Val Thr Val Thr Ser Gly Gly Thr Thr
385                 390                 395                 400

Gln Thr Phe Gln Ala Asn Ala Gly Ala Asn Leu Phe Gln Ile Pro Ala
                405                 410                 415

Ser Ile Gly Gln Gln Lys Phe Ala Leu Thr Arg Asn Gly Gln Thr Val
                420                 425                 430

Phe Ser Gly Thr Ser Leu Met Asp Ile Thr Asn Val Cys Ser Cys Gly
            435                 440                 445

Ile Tyr Asn Phe Asn Pro Tyr Val Gly Thr Ile Pro Ala Gly Phe Asp
450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
            500                 505                 510

Ser Ser Pro Pro Val Ser Ser Thr Arg Val Ser Ser Pro Pro Val Ser
        515                 520                 525

Ser Pro Pro Val Ser Arg Thr Ser Ser Pro Pro Pro Pro Ala Ser
530                 535                 540

Ser Thr Pro Pro Ser Gly Gln Val Cys Val Ala Gly Thr Val Ala Asp
545                 550                 555                 560

Gly Glu Ser Gly Asn Tyr Ile Gly Leu Cys Gln Phe Ser Cys Asn Tyr
            565                 570                 575

Gly Tyr Cys Pro Pro Gly Pro Cys Lys Cys Thr Ala Phe Gly Ala Pro
            580                 585                 590

Ile Ser Pro Pro Ala Ser Asn Gly Arg Asn Gly Cys Pro Leu Pro Gly
        595                 600                 605

Glu Gly Asp Gly Tyr Leu Gly Leu Cys Ser Phe Ser Cys Asn His Asn
610                 615                 620
```

```
Tyr Cys Pro Pro Thr Ala Cys Gln Tyr Cys
625                 630
```

(2) INFORMATION FOR SEQ ID NO: 3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer C"

(xi) SEQUENCE DESCRIPTION: SEQ ID NO: 3:

```
CATACTCGAG AAACGTGCCA GCAGCACGCC GCCATCG                          37
```

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer D"

(xi) SEQUENCE DESCRIPTION: SEQ ID NO: 4:

```
GATTACAATC ACATGACTTG GC                                          22
```

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer e"

(xi) SEQUENCE DESCRIPTION: SEQ ID NO: 5:

```
CGGAACACTC TACCGCATTA CC                                          22
```

(2) INFORMATION FOR SEQ ID NO: 6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer F"

(xi) SEQUENCE DESCRIPTION: SEQ ID NO: 6:

```
CGGCGTGCTG CTGGCAGGAA GACATGTCCC AATTAAC                          37
```

(2) INFORMATION FOR SEQ ID NO: 7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer G"

```
    (xi) SEQUENCE DESCRIPTION: SEQ ID NO: 7:

GTTAATTGGG ACATGTCTTC CTGCCAGCAG CACGCCG                                    37

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 1"

(xi) SEQUENCE DESCRIPTION: SEQ ID NO: 8:

CAGCGTCCAC ATCACGAGC                                                        19

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 2"

(xi) SEQUENCE DESCRIPTION: SEQ ID NO: 9:

GAAGAAGCAC GTTTCTGCAG AGACCG                                                26

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 3"

(xi) SEQUENCE DESCRIPTION: SEQ ID NO: 10:

CGGTCTCTCG AGAAACGTGC TTCTTC                                                26

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 4"

(xi) SEQUENCE DESCRIPTION: SEQ ID NO: 11:

GCCACTTCCG TTATTAGCC                                                        19

(2) INFORMATION FOR SEQ ID NO: 12:

(i) SEQUENCE CHARACTERISTICS:
        (A) LENGTH: 6032 base pairs
        (B) TYPE: nucleic acid
        (C) STRANDEDNESS: single
        (D) TOPOLOGY: linear (ii) MOLECULE TYPE: DNA (genomic)
```

-continued (vi) ORIGINAL SOURCE:
    (B) STRAIN: Trichoderma harzianum CBS 243.71

(ix) FEATURE:
    (A) NAME/KEY: CDS
    (B) LOCATION:3188..5092

(xi) SEQUENCE DESCRIPTION: SEQ ID NO: 12:

```
GACGAAAGGG CCTCGTGATA CGCCTATTTT TATAGGTTAA TGTCATGATA ATAATGGTTT      60
CTTAGACGTC AGGTGGCACT TTTCGGGGAA ATGTGCGCGG AACCCCTATT TGTTTATTT     120
TCTAAATACA TTCAAATATG TATCCGCTCA TGAGACAATA ACCCTGATAA ATGCTTCAA     180
AATATTGAAA AAGGAAGAGT ATGAGTATTC AACATTTCCG TGTCGCCCTT ATTCCCTTT     240
TTGCGGCATT TTGCCTTCCT GTTTTTGCTC ACCCAGAAAC GCTGGTGAAA GTAAAAGAT     300
CTGAAGATCA GTTGGGTGCA CGAGTGGGTT ACATCGAACT GGATCTCAAC AGCGGTAAG     360
TCCTTGAGAG TTTTCGCCCC GAAGAACGTT TTCCAATGAT GAGCACTTTT AAAGTTCTG     420
TATGTGGCGC GGTATTATCC CGTATTGACG CCGGGCAAGA GCAACTCGGT CGCCGCATA     480
ACTATTCTCA GAATGACTTG GTTGAGTACT CACCAGTCAC AGAAAAGCAT CTTACGGAT     540
GCATGACAGT AAGAGAATTA TGCAGTGCTG CCATAACCAT GAGTGATAAC ACTGCGGCC     600
ACTTACTTCT GACAACGATC GGAGGACCGA AGGAGCTAAC CGCTTTTTTG CACAACATG     660
GGGATCATGT AACTCGCCTT GATCGTTGGG AACCGGAGCT GAATGAAGCC ATACCAAAC     720
ACGAGCGTGA CACCACGATG CCTGTAGCAA TGGCAACAAC GTTGCGCAAA CTATTAACT     780
GCGAACTACT TACTCTAGCT TCCCGGCAAC AATTAATAGA CTGGATGGAG GCGGATAAA     840
TTGCAGGACC ACTTCTGCGC TCGGCCCTTC CGGCTGGCTG GTTTATTGCT GATAAATCT     900
GAGCCGGTGA GCGTGGGTCT CGCGGTATCA TTGCAGCACT GGGGCCAGAT GGTAAGCCC     960
CCCGTATCGT AGTTATCTAC ACGACGGGGA GTCAGGCAAC TATGGATGAA CGAAATAG    1020
AGATCGCTGA GATAGGTGCC TCACTGATTA AGCATTGGTA ACTGTCAGAC CAAGTTTA    1080
CATATATACT TTAGATTGAT TTAAAACTTC ATTTTTAATT TAAAAGGATC TAGGTGAA    1140
TCCTTTTTGA TAATCTCATG ACCAAAATCC CTTAACGTGA GTTTTCGTTC CACTGAGC    1200
CAGACCCCGT AGAAAAGATC AAAGGATCTT CTTGAGATCC TTTTTTTCTG CGCGTAAT    1260
GCTGCTTGCA AACAAAAAAA CCACCGCTAC CAGCGGTGGT TTGTTTGCCG GATCAAGA    1320
TACCAACTCT TTTTCCGAAG GTAACTGGCT TCAGCAGAGC GCAGATACCA AATACTGT    1380
TTCTAGTGTA GCCGTAGTTA GGCCACCACT TCAAGAACTC TGTAGCACCG CCTACATA    1440
TCGCTCTGCT AATCCTGTTA CCAGTGGCTG CTGCCAGTGG CGATAAGTCG TGTCTTAC    1500
GGTTGGACTC AAGACGATAG TTACCGGATA AGGCGCAGCG GTCGGGCTGA ACGGGGGG    1560
CGTGCACACA GCCCAGCTTG GAGCGAACGA CCTACACCGA ACTGAGATAC CTACAGCG    1620
AGCATTGAGA AAGCGCCACG CTTCCCGAAG GGAGAAAGGC GGACAGGTAT CCGGTAAG    1680
GCAGGGTCGG AACAGGAGAG CGCACGAGGG AGCTTCCAGG GGGAAACGCC TGGTATCT    1740
ATAGTCCTGT CGGGTTTCGC CACCTCTGAC TTGAGCGTCG ATTTTTGTGA TGCTCGTC    1800
GGGGGCGGAG CCTATGGAAA AACGCCAGCA ACGCGGCCTT TTTACGGTTC CTGGCCTT    1860
GCTGGCCTTT TGCTCACATG TTCTTTCCTG CGTTATCCCC TGATTCTGTG GATAACCG    1920
TTACCGCCTT TGAGTGAGCT GATACCGCTC GCCGCAGCCG AACGACCGAG CGCAGCGA    1980
CAGTGAGCGA GGAAGCGGAA GAGCGCCCAA TACGCAAACC GCCTCTCCCC GCGCGTTG    2040
CGATTCATTA ATGCAGCCTG ATTAATGATT ACATACGCCT CCGGGTAGTA GACCGAGC    2100
```

```
CCGAGCCAGT TCAGCGCCTA AAACGCCTTA TACAATTAAG CAGTTAAAGA AGTTAGAA 2160

TACGCTTAAA AAGCTACTTA AAAATCGATC TCGCAGTCCC GATTCGCCTA TCAAAACC 2220

TTTAAATCAA CTGATTAAAG GTGCCGAACG AGCTATAAAT GATATAACAA TATTAAAG 2280

TTAATTAGAG CAATATCAGG CCGCGCACGA AAGGCAACTT AAAAAGCGAA AGCGCTCT 2340

TAAACAGATT ACTTTTGAAA AAGGCACATC AGTATTTAAA GCCCGAATCC TTATTAAG 2400

CCGAAATCAG GCAGATAAAG CCATACAGGC AGATAGACCT CTACCTATTA AATCGGCT 2460

TAGGCGCGCT CCATCTAAAT GTTCTGGCTG TGGTGTACAG GGGCATAAAA TTACGCAC 2520

CCCGAATCGA TAGAACTACT CATTTTTATA TAGAAGTCAG AATTCATAGT GTTTTGAT 2580

TTTTAAATTT TTATATGGCG GGTGGTGGGC AACTCGCTTG CGCGGGCAAC TCGCTTAC 2640

ATTACGTTAG GGCTGATATT TACGTGAAAA TCGTCAAGGG ATGCAAGACC AAAGTAGT 2700

AACCCCGGAA GTCAACAGCA TCCAAGCCCA AGTCCTTCAC GGAGAAACCC CAGCGTCC 2760

ATCACGAGCG AAGGACCACC TCTAGGCATC GGACGCACCA TCCAATTAGA AGCAGCAA 2820

CGAAACAGCC CAAGAAAAAG GTCGGCCCGT CGGCCTTTTC TGCAACGCTG ATCACGGG 2880

GCGATCCAAC CAACACCCTC CAGAGTGACT AGGGGCGGAA ATTTAAAGGG ATTAATTT 2940

ACTCAACCAC AAATCACAGT CGTCCCCGGT ATTGTCCTGC AGAATGCAAT TTAAACTC 3000

CTGCGAATCG CTTGGATTCC CCGCCCCTAG TCGTAGAGCT TAAAGTATGT CCCTTGTC 3060

TGCGATGTAT CACAACATAT AAATACTAGC AAGGGATGCC ATGCTTGGAG TTTCCAAC 3120

AATTTACCTC TATCCACACT TCTCTTCCTT CCTCAATCCT CTATATACAC AACTGGGG 3180

CCTCACA ATG TTG GGC GTT GTC CGC CGT CTA GGC CTA GGC GCC CTT GCT   3229
        Met Leu Gly Val Val Arg Arg Leu Gly Leu Gly Ala Leu Ala
         1               5                  10

GCC GCA GCT CTG TCT TCT CTC GGC AGT GCC GCT CCC GCC AAT GTT GCT   3277
Ala Ala Ala Leu Ser Ser Leu Gly Ser Ala Ala Pro Ala Asn Val Ala
 15              20                  25                  30

ATT CGG TCT CTC GAG GAA CGT GCT TCT TCT GCT GAC CGT CTC GTA TTC   3325
Ile Arg Ser Leu Glu Glu Arg Ala Ser Ser Ala Asp Arg Leu Val Phe
             35                  40                  45

TGT CAC TTC ATG ATT GGT ATT GTT GGT GAC CGT GGC AGC TCA GCA GAC   3373
Cys His Phe Met Ile Gly Ile Val Gly Asp Arg Gly Ser Ser Ala Asp
                 50                  55                  60

TAT GAT GAT GAC ATG CAA CGT GCC AAA GCC GCT GGC ATT GAC GCA TTC   3421
Tyr Asp Asp Asp Met Gln Arg Ala Lys Ala Ala Gly Ile Asp Ala Phe
             65                  70                  75

GCT CTG AAC ATC GGC GTT GAC GGC TAT ACC GAC CAG CAA CTC GGG TAT   3469
Ala Leu Asn Ile Gly Val Asp Gly Tyr Thr Asp Gln Gln Leu Gly Tyr
         80                  85                  90

GCC TAT GAC TCT GCC GAC CGT AAT GGC ATG AAA GTC TTC ATT TCA TTC   3517
Ala Tyr Asp Ser Ala Asp Arg Asn Gly Met Lys Val Phe Ile Ser Phe
 95                 100                 105                 110

GAT TTC AAC TGG TGG AGC CCC GGT AAT GCA GTT GGT GTT GGC CAG AAG   3565
Asp Phe Asn Trp Trp Ser Pro Gly Asn Ala Val Gly Val Gly Gln Lys
                115                 120                 125

ATT GCG CAG TAT GCC AGC CGT CCC GCC CAG CTG TAT GTT GAC AAC CGG   3613
Ile Ala Gln Tyr Ala Ser Arg Pro Ala Gln Leu Tyr Val Asp Asn Arg
            130                 135                 140

CCA TTC GCC TCT TCC TTC GCT GGT GAC GGT TTG GAT GTA AAT GCG TTG   3661
Pro Phe Ala Ser Ser Phe Ala Gly Asp Gly Leu Asp Val Asn Ala Leu
        145                 150                 155

CGC TCT GCT GCA GGC TCC AAC GTT TAC TTT GTG CCC AAC TTC CAC CCT   3709
Arg Ser Ala Ala Gly Ser Asn Val Tyr Phe Val Pro Asn Phe His Pro
```

```
                160                  165                   170
GGT CAA TCT TCC CCC TCC AAC ATT GAT GGC GCC CTC AAC TGG ATG GCC3757
Gly Gln Ser Ser Pro Ser Asn Ile Asp Gly Ala Leu Asn Trp Met Ala
175                 180                 185                 190

TGG GAT AAT GAT GGA AAC AAC AAG GCA CCC AAG CCG GGC CAG ACT GTC3805
Trp Asp Asn Asp Gly Asn Asn Lys Ala Pro Lys Pro Gly Gln Thr Val
                195                 200                 205

ACG GTG GCA GAC GGT GAC AAC GCT TAC AAG AAT TGG TTG GGT GGC AAG3853
Thr Val Ala Asp Gly Asp Asn Ala Tyr Lys Asn Trp Leu Gly Gly Lys
            210                 215                 220

CCT TAC CTA GCG CCT GTC TCC CCT TGG TTT TTC ACC CAT TTT GGC CCT3901
Pro Tyr Leu Ala Pro Val Ser Pro Trp Phe Phe Thr His Phe Gly Pro
        225                 230                 235

GAA GTT TCA TAT TCC AAG AAC TGG GTC TTC CCA GGT GGT CCT CTG ATC3949
Glu Val Ser Tyr Ser Lys Asn Trp Val Phe Pro Gly Gly Pro Leu Ile
    240                 245                 250

TAT AAC CGG TGG CAA CAG GTC TTG CAG CAG GGC TTC CCC ATG GTT GAG3997
Tyr Asn Arg Trp Gln Gln Val Leu Gln Gln Gly Phe Pro Met Val Glu
255                 260                 265                 270

ATT GTT ACC TGG AAT GAC TAC GGC GAG TCT CAC TAC GTC GGT CCT CTG4045
Ile Val Thr Trp Asn Asp Tyr Gly Glu Ser His Tyr Val Gly Pro Leu
                275                 280                 285

AAG TCT AAG CAT TTC GAT GAT GGC AAC TCC AAA TGG GTC AAT GAT ATG4093
Lys Ser Lys His Phe Asp Asp Gly Asn Ser Lys Trp Val Asn Asp Met
            290                 295                 300

CCC CAT GAT GGA TTC TTG GAT CTT TCA AAG CCG TTT ATT GCT GCA TAT4141
Pro His Asp Gly Phe Leu Asp Leu Ser Lys Pro Phe Ile Ala Ala Tyr
        305                 310                 315

AAG AAC AGG GAT ACT GAT ATA TCT AAG TAT GTT CAA AAT GAG CAG CTT4189
Lys Asn Arg Asp Thr Asp Ile Ser Lys Tyr Val Gln Asn Glu Gln Leu
    320                 325                 330

GTT TAC TGG TAC CGC CGC AAC TTG AAG GCA TTG GAC TGC GAC GCC ACC4237
Val Tyr Trp Tyr Arg Arg Asn Leu Lys Ala Leu Asp Cys Asp Ala Thr
335                 340                 345                 350

GAC ACC ACC TCT AAC CGC CCG GCT AAT AAC GGA AGT GGC AAT TAC TTT4285
Asp Thr Thr Ser Asn Arg Pro Ala Asn Asn Gly Ser Gly Asn Tyr Phe
                355                 360                 365

ATG GGA CGC CCT GAT GGT TGG CAA ACT ATG GAT GAT ACC GTT TAT GTT4333
Met Gly Arg Pro Asp Gly Trp Gln Thr Met Asp Asp Thr Val Tyr Val
            370                 375                 380

GCC GCA CTT CTC AAG ACC GCC GGT AGC GTC ACG GTC ACG TCT GGC GGC4381
Ala Ala Leu Leu Lys Thr Ala Gly Ser Val Thr Val Thr Ser Gly Gly
        385                 390                 395

ACC ACT CAA ACG TTC CAG GCC AAC GCC GGA GCC AAC CTC TTC CAA ATC4429
Thr Thr Gln Thr Phe Gln Ala Asn Ala Gly Ala Asn Leu Phe Gln Ile
    400                 405                 410

CCT GCC AGC ATC GGC CAG CAA AAG TTT GCT CTA ACT CGC AAC GGT CAG4477
Pro Ala Ser Ile Gly Gln Gln Lys Phe Ala Leu Thr Arg Asn Gly Gln
415                 420                 425                 430

ACC GTC TTT AGC GGA ACC TCA TTG ATG GAT ATC ACC AAC GTT TGC TCT4525
Thr Val Phe Ser Gly Thr Ser Leu Met Asp Ile Thr Asn Val Cys Ser
                435                 440                 445

TGC GGT ATC TAC AAT TTC AAC CCA TAT GTT GGC ACC ATT CCT GCC GGC4573
Cys Gly Ile Tyr Asn Phe Asn Pro Tyr Val Gly Thr Ile Pro Ala Gly
            450                 455                 460

TTT GAC GAC CCT CTT CAG GCT GAC GGT CTT TTC TCT TTG ACC ATC GGA4621
Phe Asp Asp Pro Leu Gln Ala Asp Gly Leu Phe Ser Leu Thr Ile Gly
        465                 470                 475

TTG CAT GTC ACG ACT TGT CAG GCC AAG CCA TCT CTT GGA ACC AAC CCT4669
```

```
                Leu His Val Thr Thr Cys Gln Ala Lys Pro Ser Leu Gly Thr Asn Pro
                    480                 485                 490

CCT GTC ACT TCT GGC CCT GTG TCC TCG CTG CCA GCT TCC TCC ACC ACC   4717
Pro Val Thr Ser Gly Pro Val Ser Ser Leu Pro Ala Ser Ser Thr Thr
495                 500                 505                 510

CGC GCA TCC TCG CCT CCT GTT TCT TCA ACT CGT GTC TCT TCT CCC CCT   4765
Arg Ala Ser Ser Pro Pro Val Ser Ser Thr Arg Val Ser Ser Pro Pro
                515                 520                 525

GTC TCT TCC CCT CCA GTT TCT CGC ACC TCT TCT CCC CCT CCC CCT CCG   4813
Val Ser Ser Pro Pro Val Ser Arg Thr Ser Ser Pro Pro Pro Pro Pro
            530                 535                 540

GCC AGC AGC ACG CCG CCA TCG GGT CAG GTT TGC GTT GCC GGC ACC GTT   4861
Ala Ser Ser Thr Pro Pro Ser Gly Gln Val Cys Val Ala Gly Thr Val
        545                 550                 555

GCT GAC GGC GAG TCC GGC AAC TAC ATC GGC CTG TGC CAA TTC AGC TGC   4909
Ala Asp Gly Glu Ser Gly Asn Tyr Ile Gly Leu Cys Gln Phe Ser Cys
    560                 565                 570

AAC TAC GGT TAC TGT CCA CCG GGA CCG TGT AAG TGC ACC GCC TTT GGT   4957
Asn Tyr Gly Tyr Cys Pro Pro Gly Pro Cys Lys Cys Thr Ala Phe Gly
575                 580                 585                 590

GCT CCC ATC TCG CCA CCG GCA AGC AAT GGG CGC AAC GGC TGC CCT CTA   5005
Ala Pro Ile Ser Pro Pro Ala Ser Asn Gly Arg Asn Gly Cys Pro Leu
                595                 600                 605

CCG GGA GAA GGC GAT GGT TAT CTG GGC CTG TGC AGT TTC AGT TGT AAC   5053
Pro Gly Glu Gly Asp Gly Tyr Leu Gly Leu Cys Ser Phe Ser Cys Asn
            610                 615                 620

CAT AAT TAC TGC CCG CCA ACG GCA TGC CAA TAC TGT TAG TCTAGAGGGT    5102
His Asn Tyr Cys Pro Pro Thr Ala Cys Gln Tyr Cys *
        625                 630                 635

GACTGACACC TGGCGGTAGA CAATCAATCC ATTTCGCTAT AGTTAAAGGA TGGGGATG   5162

GGCAATTGGT TATATGATCA TGTATGTAGT GGGTGTGCAT AATAGTAGTG AAATGGAA   5222

CAAGTCATGT GATTGTAATC GACCGACGGA ATTGAGGATA TCCGGAAATA CAGACACC   5282

GAAAGCCATG GTCTTTCCTT CGTGTAGAAG ACCAGACAGA CAGTCCCTGA TTTACCCT   5342

ACAAAGCACT AGAAAATTAG CATTCCATCC TTCTCTGCTT GCTCTGCTGA TATCACTG   5402

ATTCAATGCA TAGCCATGAG CTCATCTTAG ATCCAAGCAC GTAATTCCAT AGCCGAGG   5462

CACAGTGGAG CAGCAACATT CCCCATCATT GCTTTCCCCA GGGGCCTCCC AACGACTA   5522

TCAAGAGTAT ATCTCTACCG TCCAATAGAT CGTCTTCGCT TCAAAATCTT TGACAATT   5582

AAGAGGGTCC CCATCCATCA AACCCAGTTC AATAATAGCC GAGATGCATG GTGGAGTC   5642

TTAGGCAGTA TTGCTGGAAT GTCGGGGCCA GTTGGCCGGG TGGTCATTGG CCGCCTGT   5702

TGCCATCTGC CACTAAATCC GATCATTGAT CCACCGCCCA CGAGGGCGTC TTTGCTTT   5762

GCGCGGCGTC CAGGTTCAAC TCTCTCCTCT AGCGCCTGAT GCGGTATTTT CTCCTTAC   5822

ATCTGTGCGG TATTTCACAC CGCATATGGT GCACTCTCAG TACAATCTGC TCTGATGC   5882

CATAGTTAAG CCAGCCCCGA CACCCGCCAA CACCCGCTGA CGCGCCCTGA CGGGCTTG   5942

TGCTCCCGGC ATCCGCTTAC AGACAAGCTG TGACCGTCTC CGGGAGCTGC ATGTGTCA   6002

GGTTTTCACC GTCATCACCG AAACGCGCGA                                 6032
```

(2) INFORMATION FOR SEQ ID NO: 13:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "mbd-lipase hybrid"

(ix) FEATURE:
    (A) NAME/KEY: sig_peptide
    (B) LOCATION:1..66

(ix) FEATURE:
    (A) NAME/KEY: CDS
    (B) LOCATION:1..1155

(xi) SEQUENCE DESCRIPTION: SEQ ID NO: 13:

```
ATG AGG AGC TCC CTT GTG CTG TTC TTT GTC TCT GCG TGG ACG GCC TTG   48
Met Arg Ser Ser Leu Val Leu Phe Phe Val Ser Ala Trp Thr Ala Leu
 1               5                  10                  15

GCC AGT CCT ATT CGT CGA GAG GTC TCG CAG GAT CTG TTT AAC CAG TTC   96
Ala Ser Pro Ile Arg Arg Glu Val Ser Gln Asp Leu Phe Asn Gln Phe
                20                  25                  30

AAT CTC TTT GCA CAG TAT TCT GCA GCC GCA TAC TGC GGA AAA AAC AAT  144
Asn Leu Phe Ala Gln Tyr Ser Ala Ala Ala Tyr Cys Gly Lys Asn Asn
            35                  40                  45

GAT GCC CCA GCT GGT ACA AAC ATT ACG TGC ACG GGA AAT GCC TGC CCC  192
Asp Ala Pro Ala Gly Thr Asn Ile Thr Cys Thr Gly Asn Ala Cys Pro
50                  55                  60

GAG GTA GAG AAG GCG GAT GCA ACG TTT CTC TAC TCG TTT GAA GAC TCT  240
Glu Val Glu Lys Ala Asp Ala Thr Phe Leu Tyr Ser Phe Glu Asp Ser
65                  70                  75                  80

GGA GTG GGC GAT GTC ACC GGC TTC CTT GCT CTC GAC AAC ACG AAC AAA  288
Gly Val Gly Asp Val Thr Gly Phe Leu Ala Leu Asp Asn Thr Asn Lys
                85                  90                  95

TTG ATC GTC CTC TCT TTC CGT GGC TCT CGT TCC ATA GAG AAC TGG ATC  336
Leu Ile Val Leu Ser Phe Arg Gly Ser Arg Ser Ile Glu Asn Trp Ile
                100                 105                 110

GGG AAT CTT AAC TTC GAC TTG AAA GAA ATA AAT GAC ATT TGC TCC GGC  384
Gly Asn Leu Asn Phe Asp Leu Lys Glu Ile Asn Asp Ile Cys Ser Gly
            115                 120                 125

TGC AGG GGA CAT GAC GGC TTC ACT TCG TCC TGG AGG TCT GTA GCC GAT  432
Cys Arg Gly His Asp Gly Phe Thr Ser Ser Trp Arg Ser Val Ala Asp
        130                 135                 140

ACG TTA AGG CAG AAG GTG GAG GAT GCT GTG AGG GAG CAT CCC GAC TAT  480
Thr Leu Arg Gln Lys Val Glu Asp Ala Val Arg Glu His Pro Asp Tyr
145                 150                 155                 160

CGC GTG GTG TTT ACC GGA CAT AGC TTG GGT GGT GCA TTG GCA ACT GTT  528
Arg Val Val Phe Thr Gly His Ser Leu Gly Gly Ala Leu Ala Thr Val
                165                 170                 175

GCC GGA GCA GAC CTG CGT GGA AAT GGG TAT GAT ATC GAC GTG TTT TCA  576
Ala Gly Ala Asp Leu Arg Gly Asn Gly Tyr Asp Ile Asp Val Phe Ser
            180                 185                 190

TAT GGC GCC CCC CGA GTC GGA AAC AGG GCT TTT GCA GAA TTC CTG ACC  624
Tyr Gly Ala Pro Arg Val Gly Asn Arg Ala Phe Ala Glu Phe Leu Thr
        195                 200                 205

GTA CAG ACC GGC GGA ACA CTC TAC CGC ATT ACC CAC ACC AAT GAT ATT  672
Val Gln Thr Gly Gly Thr Leu Tyr Arg Ile Thr His Thr Asn Asp Ile
    210                 215                 220

GTC CCT AGA CTC CCG CCG CGC GAA TTC GGT TAC AGC CAT TCT AGC CCA  720
Val Pro Arg Leu Pro Pro Arg Glu Phe Gly Tyr Ser His Ser Ser Pro
225                 230                 235                 240

GAG TAC TGG ATC AAA TCT GGA ACC CTT GTC CCC GTC ACC CGA AAC GAT  768
Glu Tyr Trp Ile Lys Ser Gly Thr Leu Val Pro Val Thr Arg Asn Asp
                245                 250                 255

ATC GTG AAG ATA GAA GGC ATC GAT GCC ACC GGC GGC AAT AAC CAG CCT  816
```

```
        Ile Val Lys Ile Glu Gly Ile Asp Ala Thr Gly Gly Asn Asn Gln Pro
                    260                 265                 270

AAC ATT CCG GAT ATC CCT GCG CAC CTA TGG TAC TTC GGG TTA ATT GGG  864
Asn Ile Pro Asp Ile Pro Ala His Leu Trp Tyr Phe Gly Leu Ile Gly
            275                 280                 285

ACA TGT CTT CCT GCC AGC AGC ACG CCG CCA TCG GGT CAG GTT TGC GTT  912
Thr Cys Leu Pro Ala Ser Ser Thr Pro Pro Ser Gly Gln Val Cys Val
        290                 295                 300

GCC GGC ACC GTT GCT GAC GGC GAG TCC GGC AAC TAC ATC GGC CTG TGC  960
Ala Gly Thr Val Ala Asp Gly Glu Ser Gly Asn Tyr Ile Gly Leu Cys
305                 310                 315                 320

CAA TTC AGC TGC AAC TAC GGT TAC TGT CCA CCG GGA CCG TGT AAG TGC 1008
Gln Phe Ser Cys Asn Tyr Gly Tyr Cys Pro Pro Gly Pro Cys Lys Cys
                325                 330                 335

ACC GCC TTT GGT GCT CCC ATC TCG CCA CCG GCA AGC AAT GGG CGC AAC 1056
Thr Ala Phe Gly Ala Pro Ile Ser Pro Pro Ala Ser Asn Gly Arg Asn
            340                 345                 350

GGC TGC CCT CTA CCG GGA GAA GGC GAT GGT TAT CTG GGC CTG TGG AGT 1104
Gly Cys Pro Leu Pro Gly Glu Gly Asp Gly Tyr Leu Gly Leu Trp Ser
        355                 360                 365

TTC AGT TGT AAC CAT AAT TAC TGC CCG CCA ACG GCA TGC CAA TAC TGT 1152
Phe Ser Cys Asn His Asn Tyr Cys Pro Pro Thr Ala Cys Gln Tyr Cys
    370                 375                 380

TAG                                                              1155
 *
385

(2) INFORMATION FOR SEQ ID NO: 14:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO: 14:

Met Arg Ser Ser Leu Val Leu Phe Phe Val Ser Ala Trp Thr Ala Leu
 1               5                  10                  15

Ala Ser Pro Ile Arg Arg Glu Val Ser Gln Asp Leu Phe Asn Gln Phe
                20                  25                  30

Asn Leu Phe Ala Gln Tyr Ser Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175
```

```
Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
            195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
            275                 280                 285

Thr Cys Leu Pro Ala Ser Ser Thr Pro Pro Ser Gly Gln Val Cys Val
            290                 295                 300

Ala Gly Thr Val Ala Asp Gly Glu Ser Gly Asn Tyr Ile Gly Leu Cys
305                 310                 315                 320

Gln Phe Ser Cys Asn Tyr Gly Tyr Cys Pro Pro Gly Pro Cys Lys Cys
                325                 330                 335

Thr Ala Phe Gly Ala Pro Ile Ser Pro Pro Ala Ser Asn Gly Arg Asn
            340                 345                 350

Gly Cys Pro Leu Pro Gly Glu Gly Asp Gly Tyr Leu Gly Leu Trp Ser
            355                 360                 365

Phe Ser Cys Asn His Asn Tyr Cys Pro Pro Thr Ala Cys Gln Tyr Cys
            370                 375                 380
```

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: <Unknown>

(xi) SEQUENCE DESCRIPTION: SEQ ID NO: 15:

GATCCTCACA ATGTTGGGCG TTGTCCGCCG TCTAGGCCTA GG          42

(2) INFORMATION FOR SEQ ID NO: 16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: <Unknown>

(xi) SEQUENCE DESCRIPTION: SEQ ID NO: 16:

CGCCTAGGCC TAGACGTCGG ACAACGCCCA ACATTGTGAG          40

(2) INFORMATION FOR SEQ ID NO: 17:

(i) SEQUENCE CHARACTERISTICS:
        (A) LENGTH: 11 amino acids
        (B) TYPE: amino acid
        (D) TOPOLOGY: linear -continued (ii) MOLECULE TYPE: protein (xi) SEQUENCE DESCRIPTION: SEQ ID NO: 17:

Met Leu Gly Val Val Arg Arg Leu Gly Leu Gly
                5                   10

(2) INFORMATION FOR SEQ ID NO: 18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: <Unknown>

(xi) SEQUENCE DESCRIPTION: SEQ ID NO: 18:

CCAATACTGT TAGT                              14

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: <Unknown>

(xi) SEQUENCE DESCRIPTION: SEQ ID NO: 19:

CTAGACTAAC AGTATTGGCA TG                22

(2) INFORMATION FOR SEQ ID NO: 20:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 20:

Ala Cys Gln Tyr Cys

ORAL CARE PRODUCT COMPRISING A MUTAN BINDING DOMAIN

CROSS-REFERENCE TO RELATED APPLICATIONS

This application is a continuation application of PCT/DK97/00470 filed Oct. 27, 1997 and claims priority under 35 U.S.C. 119 of Danish application 1186/96 filed Oct. 25, 1996, the contents of which are fully incorporated herein by reference.

FIELD OF THE INVENTION

The present invention relates to a polypeptide with specific binding affinity for mutan, an oral care composition comprising a polypeptide hybrid of the invention, an oral care product comprising such an oral care composition, and finally the use of a polypeptide with a specific binding affinity for mutan for oral care purposes, including preventing dental plaque formation and/or removal of existing dental plaque.

BACKGROUND OF THE INVENTION

The formation of dental plaque leads to dental caries, gingival inflammation, periodontal disease, and eventually tooth loss. Dental plaque is a mixture of bacteria, epithelial cells, leukocytes, macrophages, and other oral exudate. Said bacteria produce highly branched polysaccharides which together with micro-organisms from the oral cavity form an adhesive matrix for the continued proliferation of dental plaque.

As plaque continues to accumulate rock hard white or yellowish deposits arise. These deposits are called calcified plaque, calculus or tartar, and are formed in the saliva from plaque and minerals, such as in particular calcium.

Oral Polysaccharides

Oral polysaccharides mainly consist of the adhesive polysaccharides termed "fructans" and "glucans".

Glucans are produced from carbohydrates, such as sucrose introduced into the mouth, e.g. as a food or beverage constituent, by the action of cariogenic micro-organisms, such as *Streptococcus sobrinus* or *Streptococcus sanguis*, growing in the oral cavity.

The term "glucan" is a general common term covering a number of polysaccharides and includes cellulose, starch, dextran, mutan, pullulan etc.

Oral glucans comprise water-soluble dextran, having large portions of a-1,6 glucosidic linkage and as the major component a water-insoluble extra-cellular polysaccharide called "mutant" comprised of a backbone with a-1,3-glycosidic linkages and branches with a-1,6-glycosidic linkages.

Mutan bind to almost any surface such as the surface of teeth, (i.e. hydroxyapatite constituting the hard outer porous layer of the teeth), pellicle, the cell surface of oral micro-organisms as well as to acceptor proteins on the cell of said cariogenic bacteria adhering to the teeth surface.

WO 95/31556 (Unilever) discloses the glucan binding domain of glycosyltransferase having specificity for binding to dextran (being a polysaccharide with mainly α-1,6-glucosidic linkages).

According to WO 95/31556 the glucan binding domain is covalently chemically bound to "material" having an activity, such as inhibitory effect against the formation of dental plaque. Said material may be an enzyme, such as galactose oxidase (see Example 6).

Polysaccharide binding domains conjugated to other proteins and peptides to aid in downstream processing of recombinant fermentation are known. For instance, researchers have made fusion or hybrid proteins containing a starch binding domain (Chen et al. (1991), Gene 991, p. 121–126), cellulose binding domain (Ong et al. (1989), TIBTech 7, p. 239–243) for the purpose of purifying the proteins on starch and cellulose resins, Polysaccharide binding fusion proteins useful as removable labels (WO 93/21331).

SUMMARY OF THE INVENTION

It is the object of the present invention to provide oral care products which efficiently prevent the formation of dental plaque and/or facilitates removal of already deposited dental plaque.

In the first aspect the present invention relates to a polypeptide hybrid comprising an amino acid sequence with binding affinity for mutan, said amino acid sequence being bound to an active component useful for oral care purposes.

In the second aspect the invention relates to an oral care composition comprising a polypeptide hybrid comprising an amino acid sequence with binding affinity for mutan bound, said amino acid sequence being bound to an active component useful for oral care purposes and further ingredients conventionally used in oral care compositions.

In the third aspect the invention relates to an oral care product comprising an oral care composition of the invention.

In the final aspect the invention relates to the use of a composition of the invention or oral care product of the invention for preventing the formation of dental plaque and/or removing dental plaque.

DETAILED DESCRIPTION OF THE INVENTION

Figure 1:
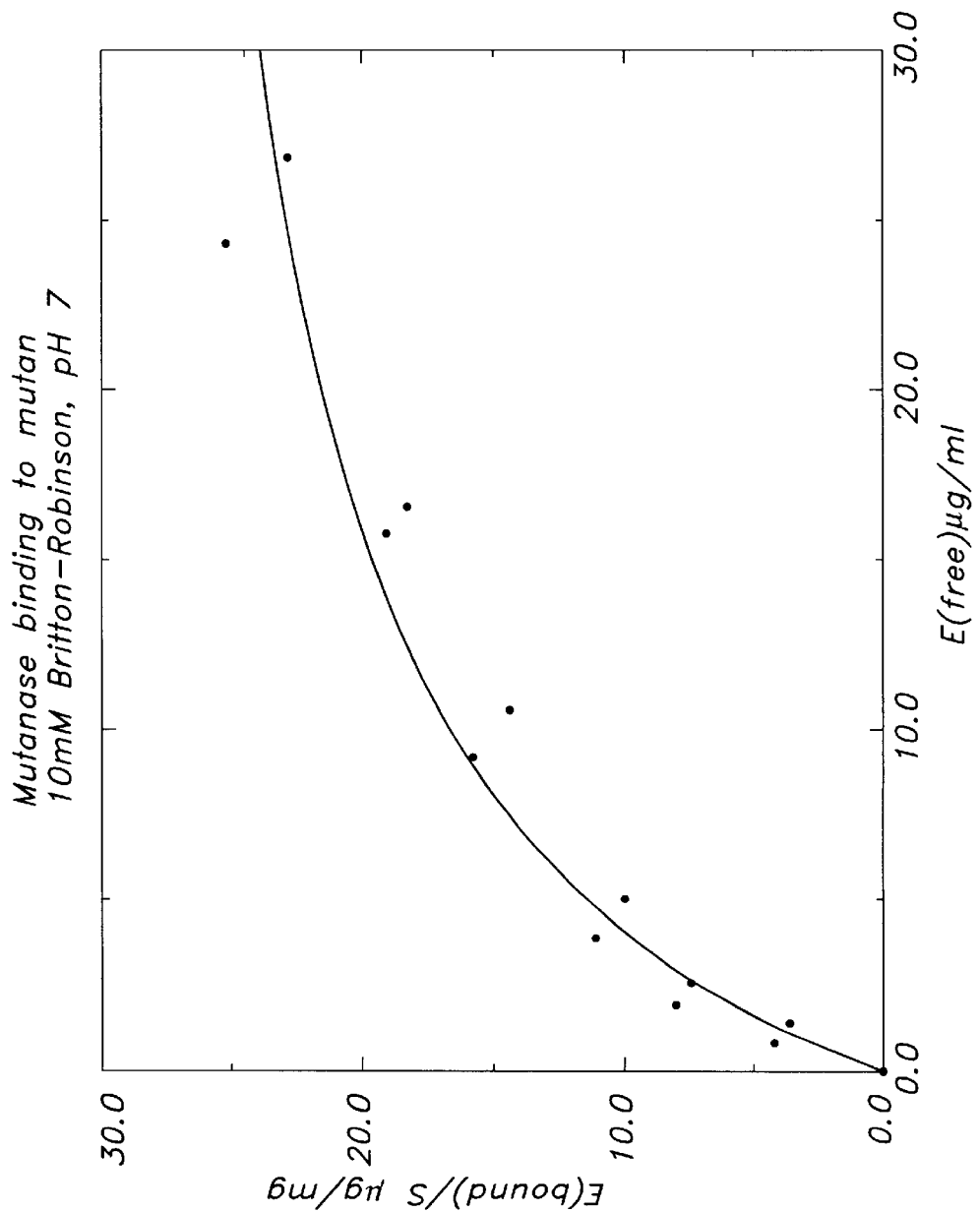
FIG. 1 shows the binding isotherm of *T. harzianum* mutanase binding to mutan.

It is the object of the present invention to provide oral care products which efficiently prevent the formation of dental plaque and/or facilitates removal of already deposited dental plaque.

The inventors of the present invention have provided polypeptide hybrids which increase the amount of active component delivered to dental plaque. This results in improved removal of dental plaque and/or in an improved dental plaque inhibiting/preventing effect when used in oral care compositions and products in comparison to the effect obtained by prior art oral care compositions and products, e.g. the composition disclosed in WO 95/31556, which delivers the active component to the dextran component of dental plaque.

The increased delivery of active component is obtained by a polypeptide (or amino acid sequence) which target(s) (i.e. binds to) the major component of dental plaque, i.e. mutan.

Said polypeptide capable of binding to mutan may be bound to an active component useful for oral care purposes to form a polypeptide hybrid.

By using a polypeptide hybrid having a binding affinity for mutan an increased amount of active component (e.g. an enzyme) is brought in close contact with the substrate (i.e. the mutan component of the dental plaque), in comparison with e.g. polypeptide hybrids which target minor components, such as the dextran component, of dental plaque.

Consequently, when targeting the dental plaque using a polypeptide hybrid capable of binding to mutan more active component (e.g. enzyme) is delivered to the place of action resulting in a more efficient processing (e.g. degradation) of oral polysaccharides and hereby removal of dental plaque. In other words the mutan binding domain of the polypeptide hybrid provides access and proximity between the active component its substrate.

Further, the dental plaque formation is more efficiently prevented as the mutan binding domain acts as a sort of competitive inhibitor blocking the binding sites to which the dental plaque forming bacteria, such as *Streptococcus sobrinus*, and glucan binding proteins, such as glucosyl-transferases (GTFs), can adhere. Consequently, a mutan binding domain may according to the present invention be a "single unit Mutan Binding Domain" as defined below.

As described in Example 12 it was found that the isolated single unit mutan binding domain binds to mutan, indicating that mutan binding domains are suitable for increasing the delivery of active component fused to the mutan binding domain to the mutan of dental plaque. Further, Example 12 also shows that single unit mutan binding domains are suitable for preventing the formation of dental plaque as the mutan binding domain when binding to mutan of dental plaque) inhibit further access of plaque forming microorganisms.

MBD

In the following "mutan binding domain" will be abbreviated as "MBD" and is meant to define all polypeptide sequences or peptide sequences having affinity for binding to mutan.

Most known MBDs today are found internally or at the N or C termini of mutanases.

As described in the Examples below, illustrating the present invention, the mutanase derived from *Trichoderma harzianum* CBS 243.71 comprises a mutan binding domain in the C-terminal end and a catalytic domain in the N-terminal end.

Single Unit Mutan Binding Domain (single unit MBD)

The term "single unit MBD" may also be referred to as "Isolated MBD" or "Separated MBD".

In the context of the present invention a "single unit MBD" includes up to the entire part of the amino acid sequence of a MBD-containing enzyme, e.g. a polysaccharide hydrolysing enzyme, being essentially free of the catalytic domain, but retaining the MBD(s).

Thus, in the context of the invention, the entire catalytic amino acid sequence of an enzyme (e.g. a mutanase) or other enzymes comprising one or more MBDs is not to be regarded as a single unit MBD.

Typically a single unit MBD constitutes one or more MBDs of a polysaccharide hydrolysing enzyme, one or more MBDs of a mutan binding protein or a protein designed and/or engineered to be capable of binding to mutan.

The single unit MBD is at least as large as the minimum number of amino acids in the amino acid sequence required to bind to mutan.

A single unit MBD may also be an amino acid sequence in which the binding and catalytic domain are one and the same.

Isolation of a MBD

In order to isolate the MBD of e.g. a mutanase, several genetic approaches may be used. One method uses restriction enzymes to remove a portion of the gene and then to fuse the remaining gene-vector fragment in frame to obtain a mutated gene that encodes a protein truncated for a particular gene fragment. Another method involves the use of exonucleases such as Ba131 to systematically delete nucleotides either externally from the 5' and the 3' ends of the DNA or internally from a restricted gap within the gene. These gene deletion methods result in a mutated gene encoding a shortened gene molecule which may then be evaluated for substrate binding ability. Appropriate substrates for evaluating the binding activity include mutan.

Once a nucleotide sequence encoding the substrate binding region has been identified, either as cDNA or chromosomal DNA, it may then be manipulated in a variety of ways to fuse it to a DNA sequence encoding the enzyme of interest. The mutan binding encoding fragment and the DNA encoding the enzyme of interest are then ligated with or without a linker. The resulting ligated DNA may then be manipulated in a variety of ways to provide for expression. Microbial hosts such as Aspergillus, e.g., *A. niger* and *A. oryzae*, Bacillus, *E. coli* or *S. cerevisiae* are preferred.

According to the invention the MBD may be bound to any active component including organic compounds, inorganic complexes, proteins, enzymes, peptides, antibodies and various ligands, which are useful for oral purposes, especially anti-plaque or anti-stain agents.

The coupling of the MBD and the active component may be performed through e.g. ester, sulfhydryl, peptide, isopeptide, amide and other types of chemical bonds.

MBD Hybrids

In the first aspect the invention relates to a polypeptide hybrid comprising an amino acid sequence with binding affinity for mutan bound to an active component useful for oral care purposes.

In an embodiment of the invention the MBD is conjugated to an enzyme to form a fusion protein or polypeptide-enzyme hybrid.

The enzyme moiety of the MBD-enzyme hybrid may be an enzyme from the following group of enzyme including oxidases, peroxidases, proteases, lipases, glucosidases, lipases, esterases, deaminases, ureases and polysaccharide hydrolases or mixtures thereof.

Example 3 to 5 described the construction, expression and purification of a MBD-enzyme hybrid constituted of the *T. harzianum* CBS 243.71 MBD fused to a *Humicola lanuginosa* lipase (Lipolase®). Other MBD-enzyme hybrids may be prepared in a corresponding way.

The above mentioned enzyme activities are preferred for oral care purposes as these activities are known to be suitable for oral care purposes. Some of the included enzyme activities are known to be capable of contributing to the degradation of different constituents of dental plaque.

Preferred as the enzyme moiety are glucosidases, preferably α-glycosidases, especially mutanases, dextranases, pullulanases and α-amylases, and mixtures thereof.

In the case of using a dextranase as the enzyme moiety it may for instance be derived from a strain of the genera Penicillium, Paecilomyces, Aspergillus, Fusarium, Spicaria, Verticillium, Helminthosporium and Chaetomium; bacteria of the genera Lactobacillus, Streptococcus, Cellvibrio, Cytophaga, Brevibacterium, Pseudomonas, Corynebacterium, Arthrobacter and Flavobacterium, and yeasts such as *Lipomyces starkeyi*.

Specifically contemplated is dextranases derived from a strain of Paecilomyces or Penicillium, such as *Paecilomyces lilacinum* or *Penicilium lilacinus*.

In the case of using a mutanase as the enzyme moiety it may for instance be derived from a strain of the genera Trichoderma, Streptomyces, Cladosporium, Bacillus, Aspergillus Specifically contemplated is mutanases derived from Trichoderma, such as *Trichoderma harziaum*, especially the deposited strain *Trichoderma harzianum* CBS 243.71.

It is preferred that the enzyme(s) is(are) substantially active at temperatures and pHs prevailing in the mouth when using the oral care product of the invention. This normally means that the enzymes should be substantially active between 20° C. and 40° C., and at pHs in the range from pH 4.0 to 8.0.

The term "substantially active" means in the context of the present invention that the enzyme in question has a relative activity above 70%, in particular above 80%, especially above 90°% of the activity at the temperature optimum.

When using a MBD-enzyme hybrid of the invention a smaller amount of enzyme need to be used to obtain the desired effect and/or less time is needed to obtain the desired effect.

Preparation of MBD Hybrids

MBD hybrids of the invention may be prepared by recombinant DNA technology e.g. as described in WO 95/16782, WO 95/31556, WO 93/21331, WO 90/00609 or other documents referred to in the "Background of the Invention" section above.

More specifically MBD hybrids may be prepared by transforming into a host cell a DNA construct comprising at least a fragment of DNA encoding the MBD ligated, with or without a linker, to a DNA sequence encoding the polypeptide, e.g. an enzyme, of interest and growing the host cell to express the fused gene. The MBD hybrids may be described by the following formula:

MBD—MR—X, wherein:
MBD can be either the N-terminal or the C-terminal region of an amino acid sequence corresponding to at least the MBD;
MR is the middle region (the linker), and may be a bond, or a short linking group of from about 2 to about 100 carbon atoms, in particular of from 2 to 40 carbon atoms, or typically from about 2 to about 100 amino acids, in particular of from 2 to 40 amino acids; and
X can be either the N-terminal or the C-terminal region and is the polypeptide of interest.

Other MBD Conjugates

The MBD hybrid may also be a conjugate of a MBD and another polypeptide, such as a non-enzymatic protein or peptide, or a chemical moiety. This will ad an additional property to the oral care composition.

The MBD may be bound to anti-plaque agents, anti-staining agents, anti-microbial agents, antibodies, antibody fragments, histamins, lactoferins, defensins, magainins, cecropins, and other cationic anti-bacteriocins and bacteriocins.

Further, the MBD may also be chemically conjugated to e.g. microbicides including, but not limited to, triclosan, chlorhexidine, quaternary ammonium compounds, chloroxylenol, chloroxyethanol, thymol, and fluoride.

Anti-microbial cat-ions such as Zn, Sn, Cu and others can also be complexed to MBDs by forming conjugates with appropriate chelating agents such as (poly)carboxylic acids, amino acids and so on.

The user of an oral care product of the invention (which will be describe in more details below), prepared from the oral care composition of the invention also described below, will benefit from the present invention, as the direct and indirect disad- vantages (e.g. yellow deposits on the teeth and prevention of dental holes and gingivitis, respectively) can be prevented more effectively than with prior art products.

Oral Care Compositions

In a second aspect the invention relates to an oral care composition comprising a MBD hybrid or single unit MBD and further ingredients conventionally used in oral care compositions.

The oral care composition of the invention may advantageously comprise MBD hybrids of the invention described above.

The enzyme moiety of the MBD-enzyme hybrids in the oral care composition may be an enzyme from the following group of enzyme including oxidases, peroxidases, proteases, lipases, glucosidases, lipases, esterases, deaminases, ureases and polysaccharide hydrolases, or mixtures thereof.

An oral care composition of the invention may suitably have incorporated an amount of 0.001–10 mg/ml MBD-hybrid calculated on the basis of final oral care product.

In a preferred embodiment the MBD hybrid is a MBD-enzyme hybrid. Preferred enzyme activities are glycosidase activities, such as an α-glycosidase activity, such as dextranase, mutanase, pullulanase and/or a-amylase activity.

In the cases of using a hybrid MBD-dextranase, MBD-mutanase, and/or MBD-pullulanase the enzyme activity should lie in the range from 0.001 KDU to 1000 KDU/ml, preferably from 0.01 KDU/ml to 500 KDU/ml, especially from 0.1 KDU/ml to 100 KDU/ml for MBD-dextranases, from 0.001 MU/ml to 1000 MU/ml, preferably from 0.01 MU/ml to 500 MU/ml, especially from 0.01 MU/ml to 100 MU/ml and from 0.01 MU/ml to 100 MU/ml, for MBD-mutanases, in the range from 0.001 KDU to 1000 KPU/ml, preferably from 0.01 KPU/ml to 500 KPU/ml, especially from 0.1 KPU/ml to 100 KPU/ml for MBD-pullulanase.

It is also contemplated according to the invention to include other enzyme activities in the oral care compositions of the invention. Contemplated enzymes, beside dextranase and mutanase, may be from the group including proteases, such as papain, endoglucosidases, lipases, amylase and mixtures thereof.

Oral Care Products

The invention also relates to oral care products comprising an oral care composition of the invention. The oral care product may have any suitable physical form (i.e. powder, paste, gel, liquid, ointment, tablet etc.). An "oral care product" can be defined as a product which can be used for maintaining or improving the oral hygiene in the mouth of humans and animals, by preventing formation of dental plaque, removing dental plaque, preventing and/or treating dental diseases etc.

At least in the context of the present invention, oral care products also encompass products for cleaning dentures, artificial teeth and the like.

Examples of such oral care products include toothpaste, dental cream, gel or tooth powder, odontic, mouth washes, pre- or post brushing rinse formulations, chewing gum, lozenges, and candy.

Toothpastes and tooth gels typically include abrasive polishing materials, foaming agents, flavouring agents, humectants, binders, thickeners, sweetening agents, whitening/bleaching/ stain removing agents, water, and optionally enzymes.

Mouth washes, including plaque removing liquids, typically comprise a water/alcohol solution, flavor, humectant, sweetener, foaming agent, colorant, and optionally enzymes.

Abrasive polishing material might also be incorporated into the dentifrice product of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care product the abrasive product may be present in from 0 to 70% by weight, preferably from 1% to 70%. For toothpastes the abrasive material content typically lies in the range of from 10% to 70% by weight of the final toothpaste product.

Humectants are employed to prevent loss of water from e.g. toothpastes. Suitable humectants for use in oral care products according to the invention include the following compounds and mixtures thereof: glycerol, polyol, sorbitol, polyethylene glycols (PEG), propylene glycol, 1,3-propanediol, 1,4-butanediol, hydrogenated partially hydrolysed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing the dentifrice product. Thickeners may be present in toothpaste creams and gels in an amount of from 0.1 to 20% by weight, and binders to the extent of from 0.01 to 10% by weight of the final product.

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants are only suitable to the extent that they do not exert an inactivation effect on the present MBD hybrids. Surfactants include fatty alcohol sulphates, salts of sulphonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin.

Flavors, such as spearmint, are usually present in low amounts, such as from 0.01% to about 5% by weight, especially from 0.1% to 5%.

Whitening/bleaching agents include $H_2O_2$ and may be added in amounts less that 5%, preferably from 0.25 to 4%, calculated on the basis of the weight of the final product.

Water is usually added in an amount giving e.g. toothpaste a flowable form.

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of compounds which can be used as fluoride source, dyes/colorants, preservatives, vitamins, pH-adjusting agents, anti-caries agents, desensitizing agents etc.

Other essential components used in oral care products and in oral care products of the invention are enzymes. Enzymes are biological catalysts of chemical reactions in living systems. Enzymes combine with the substrates on which they act forming an intermediate enzyme-substrate complex. This complex is then converted to a reaction product and a liberated enzyme which continue its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes. Dextranase breaks down the organic skeletal structure produced by bacteria that forms a matrix for bacterial adhesion. Proteases and amylases, not only prevents plaque formation, but also prevents the development of calculus by breaking-up the carbohydrate-protein complex that binds calcium, preventing mineralization.

A toothpaste produced from an oral care composition of the invention (in weight % of the final toothpaste composition) may typically comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Whitener | 0 to 5% |
| Enzymes | 0 to 20% |
| MBD hybrid and/or single unit MBD | 0.0001% to 1% |

In a specific embodiment of the invention the oral care product is comprising

| | | |
|---|---|---|
| a) | 10% to 70% | Abrasive material |
| b) | 0 to 80% | Humectant |
| c) | 0.1 to 20% | Thickener |
| d) | 0.01 to 10% | Binder |
| e) | 0.1% to 5% | Sweetener |
| f) | 0 to 15% | Foaming agent |
| g) | 0 to 5% | Whitener |
| i) | 0 to 20% | Enzymes |
| j) | 0.0001% to 1% | MBD hybrid and/or single unit MBD |

Said MBD hybrid referred to in connection with the specific toothpaste and mouth wash above may have any activity, such as enzymatic activity, suitable for oral care purposes. Preferred enzyme activities are a-glycosidases, especially dextranases, mutanases, pullulanases, and a-amylases. Said enzyme referred to include all enzyme activities suitable in oral care products.

Use of an Oral Care Composition or Product

In the third aspect the invention relates to the use of the composition of the invention or an oral care product of the invention for preventing the formation of plaque and/or for removing dental plaque.

Method of Manufacture

The oral care composition and products of the present invention can be made using methods which are common in the oral product area.

MATERIALS AND METHODS

Materials

Enzymes

Mutanase produced by *Trichoderma harzianum* CBS 243.71 (available from Novo Nordisk A/S)

*Humicola lanuginosa* lipase (available from Novo Nordisk A/S as Lipolase®) and is described in EP 305 216.

Plasmids:

pAHL: a *Humicola lanuginosa* lipase gene (sometimes referred to as lipolase gene) containing plasmid described in EP 305,216. pMT1796: mutanase expression plasmid prepared as described in Example 8.

pHD414: Aspergillus expression vector is a derivative of the plasmid p775 (described in EP 238.023). The construction of the pHD414 is further described in WO 93/11249. pHD414 contains the *A. niger* glucoamylase terminator and the *A. oryzae* TAKA amylase promoter.

pHD414+mut (pHD414 comprising the *T. harzianum* mutanase gene) pHan37 containing the TAKA:TPI promoter Linkers:

```
Linker #1:
GATCCTCACA ATG TTG GGC GTT GTC CGC CGT CTA GGC CTA GG       SEQ ID NO:15
    GAGTGT TAC AAC CCG CAA CAG GCT GCA GAT CCG GAT CCG C    SEQ ID NO:16
           Met Leu Gly Val Val Arg Arg Leu Gly Leu Gly      SEQ ID NO:17

Linker #2:
         C CAA TAC TGT TAG T      SEQ ID NO:18
    GT ACG GTT ATG ACA ATC AGATC  SEQ ID NO:19
       Ala Cys Gln Tyr Cys ***    SEQ ID NO:20
```

Micro-organisms:

*Trichoderma harzianum* CBS 243.71

*Streptococcus sobrinus* strain CBS 350.71 identifiable as OMZ 176

*Actinomyces viscosus* DSM 43329

*Fusobacterium nucleatum* subsp. polymorphum DSM 20482

*A. oryzae* JaL125: *Aspergillus oryzae* host strain with the alkaline protease gene named "alp" deleted. Strain JaL125 is disclosed in WO 97/35956 (Novo Nordisk A/S)

Solutions and the Like

Britton-Robinson Buffer

CAPS (3-cyclohexylamino-1-propanesulfonic acid) (Sigma)

Coomassie Brilliant Blue R250(Sigma)

Peroxidase-conjugated swine immunoglobulins (DAKO, Denmark)

Erythrosin B (Sigma)

Equipment

Shaker (Eppndorf Thermomixer, Type 5436)

473A Protein Sequencer from Applied Biosystems

SDS-PAGE 4–20% (Novex)

Tricine 16% gel (Novex)

Tris-Glycine 4–20% (Novex)

Immobolin $P^{SQ}$ PVDF membrane (Millipore)

Chromameter CR-200 (Minolta)

Preparation of Hydroxyapatite Disks

Hydroxyapatite (HA) disks are prepared by compressing 250 mg of hydroxyapatite in a disk die at about 5,900 kg (13,000 lbs) of pressure for 5 minutes. The disks are then sintered at 600° C. for 4 hours and finally hydrated with sterile deionized water.

Sterilisation of Hydroxyapatite Disks

HA disks are sterilised at 180° C. for two hours.

Preparation of Mutan

Mutan is prepared by growing Streptococcus sobrinus CBS 350.71 at pH 6.5, 37° C. (kept constant), and with an aeration rate of 75 rpm in a medium comprised of the following components:

| | |
|---|---|
| NZ-Case | 6.5 g/liter |
| Yeast Extract | 6 g/liter |
| $(NH_4)_2SO_4$ | 20 g/liter |
| $K_2PO_4$ | 3 g/liter |
| Glucose | 50 g/liter |
| Pluronic PE6100 | 0.1% |

After 35 hours, sucrose is added to a final concentration of 60 g/liter to induce glucosyltransferase. The total fermentation time is 75 hours. The supernatant from the fermentation is centrifuged and filtered (sterile). Sucrose is then added to the supernatant to a final concentration of 5% (pH is adjusted to pH 7.0 with acetic acid) and the solution is stirred overnight at 37° C. The solution is filtered and the insoluble mutan is harvested on propex and washed extensively with deionized water containing 1% sodium benzoate, pH 5 (adjusted with acetic acid). Finally, the insoluble mutan is lyophilized and ground.

Methods

Molecular Biology Procedures

All molecular biology procedures including restriction digests, DNA ligations, *E. coli* transformations, DNA isolations, Southern hybridizations, PCR amplifications, and library constructions and screenings were completed using standard techniques (Sambrook, J., Fritsch, E. F., and Maniatis, T. 1989. *Molecular cloning: A laboratory manual/* E. F. Cold Spring Harbor Laboratory Press, Plainview, N.Y.).

Determination of Dextranase Activity (KDU)

One Kilo Novo Dextranase Unit (1 KDU) is the amount of enzyme which breaks down dextran forming reducing sugar equivalent to 1 g maltose per hour in Novo Nordisk' method for determination of dextranase based on the following standard conditions:

| Substrate | Dextran 500 (Pharmacia) |
|---|---|
| Reaction time | 20 minutes |
| Temperature | 40° C. |
| pH | 5.4 |

A detailed description of Novo Nordisk's analytical method (AF 120) is available on request.

Determination of Mutanase Activity (MU)

One Mutanase Unit (MU) is the amount of enzyme which under standard conditions liberates 1 mmol reducing sugar (calculated as glucose) per minute.

Standard Conditions

| Substrate | 1.5% mutan |
|---|---|
| Reaction time | 15 minutes |
| Temperature | 40° C. |
| pH | 5.5 |

A detailed description of Novo Nordisk's analytical method (AF 180/1-GB) is available from Novo Nordisk A/S on request.

Preparation of Mutan Adhered Glass Wall

*Streptococcus sobrinus* OMZ 176 (CBS 350.71) is inoculated in a glass tube (22 mm diameter×150 mm height) containing 10 ml Todd Hewitt Broth with 2% sucrose and the tube is allowed to stand overnight at 37° C. The broth is discarded and adhered mutan and Streptococcus sobrinus cells on glass wall are washed twice with 10 ml of 0.85% NaCl solution.

Langmuir Fit $$A=(Amax*E)/((1/K(ads)+E)$$

A: Adsorbed enzyme
E: Free enzyme
Amax: Max adsorbed enzyme
K(ads): Adsorption coefficient The Langmuir fit is described in Stuart, J. Y. & Ristoph, D. L., (1984), Biotechnol. Bioengng, 27, p 1056+.

Assessment of the Plaque Inhibition Effect

The method used for assessing the plaque removal effect is based on the method described by Kao in JP 2250816. According to the present method the hydroxyapatite disks, sterilised as described above, become coated with a biofilm by being placed overnight in the presence of three strains of oral micro-organisms (*Streptococcus sobrinus, Actinomyces viscosus* and *Fusobacterium nucleatum*) and various enzymes in a Brain Heart Infusion Medium (Difco) containing 0.2% sucrose.

To test plaque inhibition effect, 0.1% Erythrosin B in PBS (phosphate buffered saline) is used to stain plaque present on the hydroxyapatite disks red. The intensity of the red colour (referred to as a*) is measured on a Chromameter CR-200. The maximum a* value is 60. Values below that indicate a less intensive red colour (i.e. less plaque present). An a* value of zero indicated no red colouring (i.e. no plaque). A plaque inhibition effect is expressed as a relative figure based on the value of a* for a non-treated biofilm being 100%.

EXAMPLES

Example 1

Binding of Purified Mutanase to Mutan

The binding of purified *T. harzianum* CBS 243.71 mutanase (SEQ ID NO. 2) to mutan was investigated by incubating mutanase in varying concentration with 1 mg/ml mutan in 10 mM Britton-Robinson buffer, pH 7, at 4° C. for 1 hour while stirring. The samples were then centrifuged at 15,000 g for 2.5 minutes and filtered through 0.45 micrometer filters (Millipore). The residual activity was measured in the supernatant. The binding isotherm obtained can be fitted to simple Langmuir binding and an affinity constant and a max adsorption constant can be obtained. FIG. 1 displays the result of the test. As can be seen the mutanase binds to mutan.

Example 2

Construction of the Recombinant Mutanase Expression Vector pMT1796

A cDNA clone encoding mutanase was identified in a *Trichoderma harzianum* CBS 243.71 library by hybridization with a fragment of the mutanase gene amplified by PCR using primers based on the mutanase sequence shown in SEQ ID NO. 1.

DNA sequence analysis of the isolated clone, pHD414+mut, showed that it indeed encoded the mutanase gene, and that the 5' end of the construct contained a long leader sequence. To remove this leader, pHD414+mut was restricted with the enzymes EcoRI, NarI and XhoI. From this digestion a 3499 nt (nucleotide) vector fragment and a 610 nt NarI/XhoI fragment were isolated. These two fragments were then ligated with linker #1 (see above) and a 618 nt EcoRI/BamHI fragment from pHan37 containing the TAKA:TPI promoter, giving plasmid pJW99. HD414+mut was next digested with XhoI and SphI, and a 1790 nt fragment encoding amino acids 35–598 of the mutanase gene was isolated.

This fragment was ligated with linker #2 (see above) and pJW99 that had been linearized with the restriction enzymes XbaI and XhoI. The resulting plasmid, pMT1802, contains the *T. harzianum* mutanase gene under the control of the TAKA:TPI promoter. Plasmid pMT1796 is identical to pMT1802 except that E36 of the mutanase protein has been changed to K36 by replacing the XhoI/KpnI fragment of pMT1802 with a PCR amplified fragment containing the desired mutation.

This PCR fragment was created in a two step procedure as reported in Ho, et al. (1989), Gene, 77, p. 51–59, using the following primers:

Primer 1 (SEQ ID No. 8):
(nt 2751 5' CAGCGTCCACATCACGAGC nt 2769); and

Primer 2 (SEQ ID No. 9)
(nt 3306 5' GAAGAAGCACGTTTCTC-GAGAGACCG nt 3281);

Primer 3 (SEQ ID NO. 10)
(nt 3281 5' CGGTCTCTGAGAAACGTGCTTCTTC nt 3306) and

Primer 4 (SE ID No. 11)

(nt 4266 5' GCCACTTCCGTTATTAGCC nt 4248); nucleotide numbers refer to the pMT1802 plasmid (See SEQ ID No. 12).

Example 3

Construction of Recombinant MBD-lipase Hybrid A. Oryzae Expression Plasmid pJW105

Figure 2:
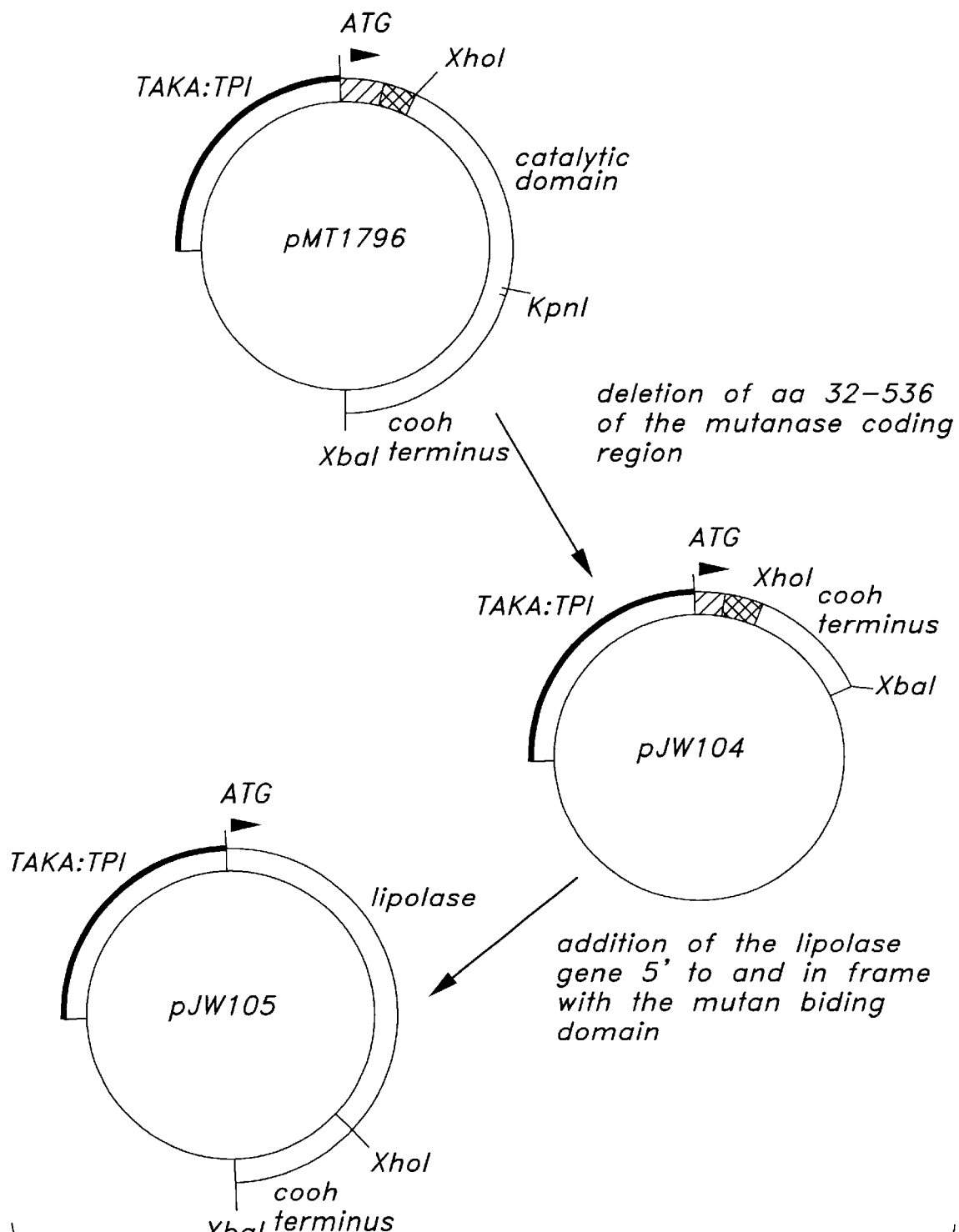
FIG. 2 shows lineage of the mutanase constructs pMT1796, pJW104 and pJW105. Regions of the plasmids are labelled as follows: the lipase and mutanase genes as open boxes; the mutan binding domain as "cooh terminus"; a thick-lined arc= promoter; an arrow signifies the direction of transcription; ø= mutanese signal sequence; ■= mutanese prosequence; restriction enzyme sites are labelled.

Construction of pJW104 (DNA construct with a mutan binding domain)

pJW104 containing an internal deletion of the mutanase coding region encompassing amino acids 32–536 (nt 94–1608) was constructed as follows:

The mutanase expression plasmid, pMT1796 (described in Example 2), contains two unique restriction sites which were used in the construction of pJW104: a XhoI site that sits 6 nucleaotides 5' to the first codon of the mature protein and an XbaI site that immediately follows that stop codon (see FIG. 2).

A primer, Primer C (SEQ ID No. 3), was made. The 3' end of this primer consists of 21 nucleotides matching the sequence of the mutanase gene corresponding to aminoacid 537 to 543 in the sense direction. The 5' end of the primer harbors a XhoI site. Primer C:

```
5'CATACTCGAGAAACGT GCC AGC AGC ACG CCG CCA TCG 3'
    Xho I        Ala Ser Ser Thr Pro Pro Ser
                                         537
```

Another primer, Primer D (SEQ ID No. 4), was made. This primer match a sequence of pMT1796 downstream from the XbaI site, and oriented in the opposite direction of primer C. Primer D:

5' GATTACAATCACATGACTTGGC 3' pMT 1796 was PCR amplified using the primers C and D. Digestion of the 433 nt amplicon with XhoI and XbaI yielded a fragment of 290 nt that was cloned into pMT1796 that had been linearized with these same two enzymes. Altered regions of pJW104 were DNA sequences to confirm the presence of the deletion and to check the integrity of the mutanase gene.

Construction of pJW105

Figure 3:
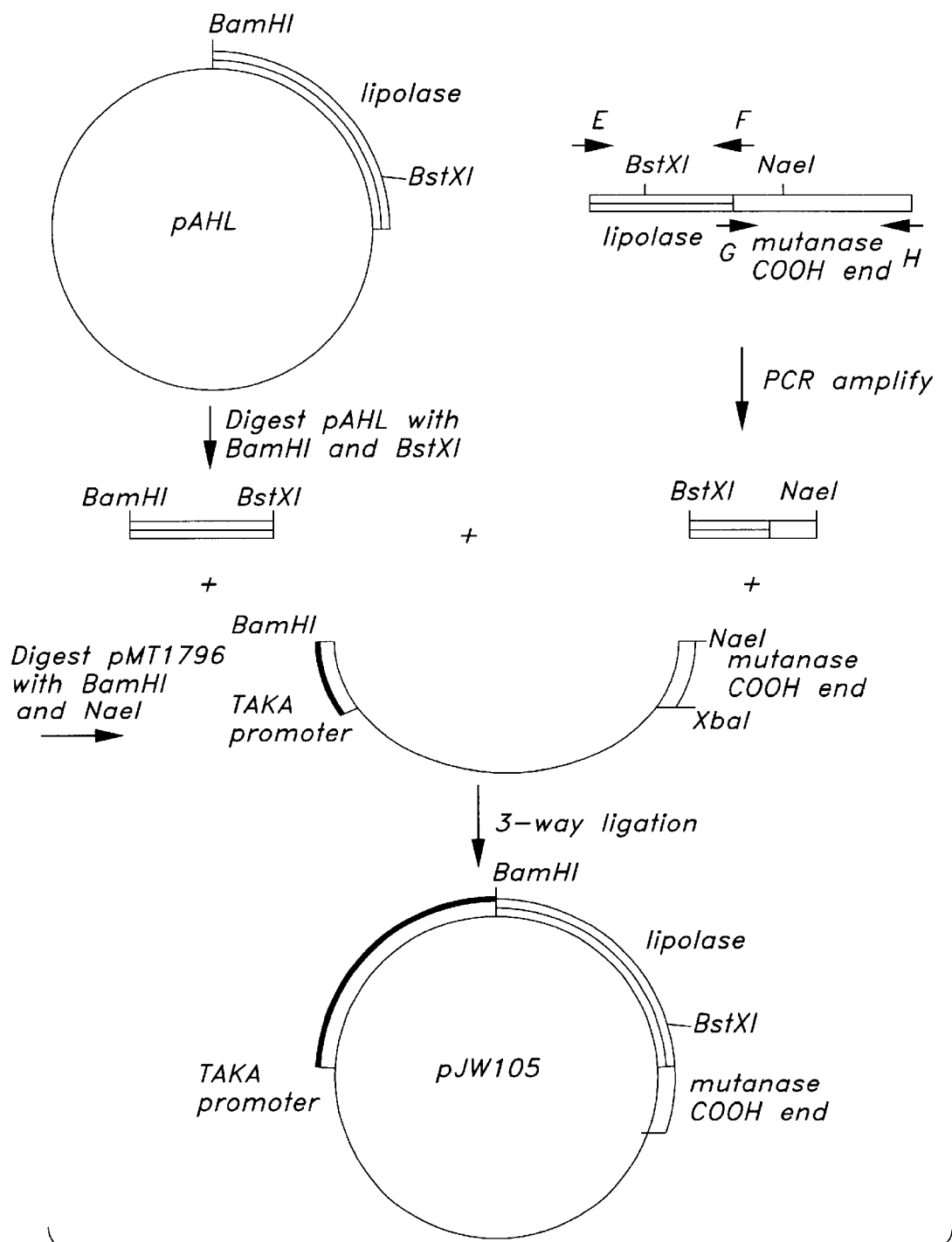
FIG. 3 outlines the construction of the expression plasmid pJW105. Regions are marked as follows: the *Humicola lanuginose* lipase gene (lipolase gene) as a striped box; the mutanese gene as an open box; primers by an arrow indicating their 5' to 3' orientation; the TAKA promoter by a heavy-line; restriction enzyme sites are labelled.

To create pJW105, three DNA fragments (shown in FIG. 3) were ligated: a vector fragment from pMT1796, a fragments containing the amino portion of the *Humicola lanuginosa* lipase gene, and a PCR amplicon containing the in-frame fusion between the COOH terminus of the *Humicola lanuginosa* lipase gene and the MBD of *T. harzianum* mutanase. pMT1796 contains two unique restriction enzyme sites, a BamHI fragment that sits at the 3' end of the TAKA promoter just before the initiating Met and a NaeI site that sits over codons 425 and 426 in the COOH terminus of mutanase gene. Digestion of the plasmid with these two enzymes gives a 4359 nt fragment that was gel purified. The *Humicola lanuginosa* lipase gene portion of the construct is a 727 nt BamHI/BstXI restriction fragment from the expression plasmid pAHL. The unique BamHI site within this plasmid lies immediately 5' to the start codon of the gene, and the unique BstXI site lies over codons 214–216 of the mature *Humicola lanuginosa* lipase protein. The final piece of the construct was created using overlap-PCR-extension (Ho et al. (1989), Gene, 77, 51–59) with two rounds of PCR amplification and the primers E, F, G and further Primer D (see above):

Primer E (SEQ ID No. 5):
5' CGGAACACTCTACCGCATTACC 3'

Primer F (SEQ ID No. 6):
5' CGGCGTGCTGCTGGCAGGAAGACATGTC-CCAATTAAC 3',

Primer G (SEQ ID No. 7)
5' GTTAATTGGGACATGTCTTCCTGCCAG-CAGCACGCCG 3'

Primers F and G overlap the *Humicola lanuginosa* lipase/mutanase fusion of the construct. First round amplification consisted of two separate reactions one of which paired primers E and F with the lipase plasmid pAHL, and the second that paired primers G and D with the mutanase plasmid pMT1796. This reaction yielded fragments of 237 and 449 nt, respectively. Second round amplification paired primers E and D with 0.25 ml of the reaction mixtures from the amplification round 1. The resulting 670 nt fragment was digested with BstXI and NaeI, gel purified and ligated together with the vector fragment and the 727 nt BamHI/BstXI fragment from the lipase gene. The protein coding region of the resulting plasmid, pJW105, was DNA sequenced.

The DNA and amino acid sequence of the MBD-lipase hybrid is shown in SEQ ID No. 13 and 14, respectively.

Example 4

Expression of Recombinant MBD-lipase Hybrid in *Aspergillus oryzae*

0.1 µg pJW105 was transformed into *A. oryzae* strain JaL125 using a PEG-mediated protocol (see EP 238,023) and a DNA mixture containing 0.5 µg of a plasmid encoding the gene that confers resistance to the herbicide Basta. Transformants were selected on minimal plates containing 0.5% basta and 50 mM urea as a nitrogen source.

Shake Flask Cultures

Transformed colonies were spore purified twice on selection media and spores were harvested. A 20 ml universal container (Nunc, cat #364211) containing 10 ml YPM (2% maltose, 1% bactopeptone and 0.5% yeast extract) was inoculated with spores and grown for 5 days with shaking at 30° C. The supernatant was harvested after 5 days growth.

SDS-PAGE and protein transfers were performed using standard protocols.

Example 5

Purification of the Recombinant MBD-lipase Hybrid

Purification of the recombinant MBD-lipase hybrid from the *A. oryzae* JaL125 fermentation broth was peformed as follows: Filtered fermentation broth was incubated with 5% mutan in 0.1% sodium acetate, pH 5.5, for 30 minutes while stirring. The sample was centrifuged for 10 minutes at 10,000 g. The precipitate was re-suspended in 1 ml 0.1 M sodium acetate, pH 5.5, and centrifuged. This step was repeated 3 times before eluting the MBD with water (MilliQ-filtered). The eluate was concentrated on an Amicon cell (YM10 membrane). The fusion protein (i.e. the MBD hybrid) was further purified by gel filtration using a Superdex75 16/60 column (Pharmacia) in 0.1 M sodium acetate, pH 6 hybrid.

Example 6

Binding of Recombinant MBD-lipase Hybrid to Mutan

The binding of purified MBD-lipase hybrid (SEQ ID NO. 14) to mutan is investigated using the procedure described in Example 1.

Example 7

Expression of Recombinant Single unit MBD in Aspergillus oryzae

Expression of the A. oryzae expression plasmid pJW104 coding for the single unit MBD of the T. harzianum mutanase was carried out as described in Example 4.

Example 8

Purification of the Recombinant Single Unit MED

Isolated MBD was purified by incubating 30 ml fermentation broth of A. orzyae expressing the C-terminal domain of the mutanase with 3 ml 5% mutan in 0.1 sodium acetate, pH 5.5, for 30 minutes while stirring.

The sample was centrifuged for 10 minutes at 10,000 g. The precipitate was re-suspended in 1 ml 0.1 M sodium acetate, pH 5.5, and centrifuged. This step was repeated 3 times before eluting the MBD with water (MilliQ-filtered). Purified MBD appeared at a molecular weight around 10 kDa in westerns.

Example 9

Immuno Detection of MBD

The MBD can be detected by Mancini immuno diffusion. 12 ml of 1% agarose in 20 mM Tris-Maleate, pH 7, at 56° C. was added 100 µl of mutanase antibodies raised in rabbits. The solution was poured onto GelBond Film. 10 µl samples were added to each well and the gel was left over night at room temperature. The gel was then washed in 0.5% NaCl and 3 times in water before drying. The gel was stained in 0.5% Coomassie Brilliant Blue 45% ethanol, 10% acetic acid for 1 minute and de-stained in 25% ethanol, 10% acetic acid.

Example 10

Western Analysis of MED, Catalytic Domain and Humicola Lanuginosa Lipase-MBD Fusion Protein SDS-PAGE was performed using a Tricine 16% gel from Novex (for the MBD) or Tris-Glycine 4–20% (Novex) (for higher $M_w$ proteins). The proteins were blotted onto a Millipore Immobolin $P^{SQ}$ PVDF membrane in 10 mM glycine, 20% methanol, pH 11.8 at 175 mA for 3 hours. Standards and controls were Coomassie stained (see Example 9) while the rest of the membrane was blocked with 4.875 ml Tween2o in 245 ml washing solution (30.3 g Tris base, 43.8 g NaCl, 2.5 ml Tween20 in 5 litre water) for 3 minutes before washing with the washing solution. The membrane was then reacted with 50 µl of the detecting antibodies (mutanase antibodies raised in rabbits) diluted to 50 ml with washing solution and washed 4 times with washing solution before incubating with peroxidase-conjugated swine immunoglobulins to rabbit immunoglobulins (50 µl in 50 ml washing solution). The membrane was washed again with washing solution and once with 50 mM sodium acetate, pH 5, and stained with carbazol (2 ml 3-amino-9-ethylcarbazol in 48 ml acetate buffer added 25 µl 30% $H_2O_2$). The membrane was then washed in water and fixed in 12.4 g sodium thiosulfate in 1 litre of water.

Example 11

Isolation of Single Unit MBD of T. Harzianum

Single unit MBD of T. harzianum CBS 243.71 was isolated by proteolytic degradation of mutanase.

Purified T. harzianum mutanase was digested with chymoptrypsin in a ratio of 1:100 (protease:mutanase) in 0.1 M Tris-HCl buffer, pH 8.5 at 30° C. for 2.5 hours. The resulting digest was investigated using SDS-PAGE (Novex 4–20%). The 42 kDa band observed was blotted onto a Millipore Immobolin PSQ PVDF membrane in 10 mM CAPS, 6% methanol at 175 mA for 3 hours. The membrane was stained with 0.1% Coomassie Brilliant Blue R250 in 60% methanol, 1% acetic acid and destained in 40% methanol. The 42 kDa band was subjected to N-terminal amino acid sequencing using the 473A Protein Sequencer from Applied Biosystems according to the manufacturer's description.

The N-terminal sequence obtained was Ser-Leu-Thr-Ile-Gly-Leu corresponding to a proteolytic cleavage between Phe436 and Ser437 (see SEQ ID NO. 1 or 2) in the mature mutanase. The C-terminal domain obtained by chymotrypsin digestion was shown to bind to mutan by incubating the 50 µl chymotrypsin digest with 50 µl 5% mutan in 0.1 M ammonium bicarbonate, pH 8.15 for 30 minutes at 25° C. The sample was then centrifuged for 5 minutes at 15,000 g and 30 µl sample was then loaded onto SDS-PAGE (Novex 4–20%). A control without mutan (buffer) was included.

Example 12

Binding of Purified MBD to Mutan

The single unit MBD was mixed 1:1 with 0.1 M acetate buffer, pH 5.5 with/without 5% mutan. The samples were incubated for 30 minutes at room temperature before centrifuging the samples 5 minutes at 15,000 g. 10 µl of supernatant was analysed by Mancini immuno diffusion. No MBD was detected in the sample pre-incubated with mutan indicating that the single unit MBD binds to mutan.

Example 13

Catalytic Domain

Fermentation broth of A. oryzae expressing the N-terminal domain of the mutanase was analysed for. It was observed that said N-terminal domain has catalytic activity.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

---

What is claimed is:

1. A hybrid comprising:
   (a) a peptide sequence within SEQ ID NO:2, which has a binding affinity for mutan and lacks a functional catalytic domain of SEQ ID NO:2; linked to
   (b) an enzyme selected from the group consisting of deaminases, esterases, glucosidases, lipases, oxidases, peroxidases, polysaccharide hydrolases, proteases, and ureases.

2. The hybrid of claim 1, wherein the peptide sequence comprises amino acid residues 537–634 of SEQ ID NO:2.

3. The bybrid of claim 1, wherein the peptide sequence consists of amino acid residues 537–634 of SEQ ID NO:2.

4. The hybrid of claim 1, wherein the enzyme is a glycosidase.

5. An oral care composition comprising (a) a hybrid of claim 1 and (b) further ingredients conventionally used in oral care compositions.

6. The oral care composition of claim 5, wherein the hybrid comprises amino acid residues 537–634 of SEQ ID NO:2.

7. An oral care product comprising an oral care composition of claim 5.

8. The oral care product of claim 7, which is a dentifrice.

* * * * *